(12) United States Patent
Konkle et al.

(10) Patent No.: US 8,766,200 B2
(45) Date of Patent: Jul. 1, 2014

(54) MECHANICAL SHOCK ISOLATION FOR A RADIOGRAPHIC DEVICE

(75) Inventors: Nicholas Ryan Konkle, Waukesha, WI (US); Christopher Jay Morse, North Prairie, WI (US)

(73) Assignee: General Electric Company, Schenectady, NY (US)

( * ) Notice: Subject to any disclaimer, the term of this patent is extended or adjusted under 35 U.S.C. 154(b) by 269 days.

(21) Appl. No.: 13/342,745

(22) Filed: Jan. 3, 2012

(65) Prior Publication Data
US 2013/0168564 A1 Jul. 4, 2013

(51) Int. Cl.
| G01T 1/16 | (2006.01) |
| A61B 6/10 | (2006.01) |
| G01T 1/00 | (2006.01) |
| A61B 6/00 | (2006.01) |

(52) U.S. Cl.
CPC . *A61B 6/102* (2013.01); *G01T 1/00* (2013.01); *A61B 6/4405* (2013.01); *A61B 6/4283* (2013.01)
USPC .................................. 250/370.08; 250/370.09

(58) Field of Classification Search
CPC .......... G01T 1/00; G03B 42/02; G03B 42/04; A61B 6/102; A61B 6/4233; A61B 6/4283; A61B 6/4405; A61B 6/4429
USPC .............. 250/370.01, 370.08, 370.09, 370.11
See application file for complete search history.

(56) References Cited

U.S. PATENT DOCUMENTS

| | | | |
|---|---|---|---|
| 5,204,832 A | 4/1993 | Nakakura | |
| 5,912,944 A * | 6/1999 | Budinski et al. | 378/182 |
| 6,025,598 A | 2/2000 | Tago | |
| 6,700,126 B2 | 3/2004 | Watanabe | |
| 6,825,472 B2 | 11/2004 | Endo | |
| 6,897,449 B1 | 5/2005 | Hata | |
| 7,057,181 B2 | 6/2006 | Yagi | |
| 7,189,972 B2 | 3/2007 | Ertel et al. | |
| 7,317,190 B2 | 1/2008 | Ertel et al. | |
| 7,397,037 B2 | 7/2008 | Watanabe | |
| 7,488,946 B2 | 2/2009 | Hennessy et al. | |
| 7,495,226 B2 | 2/2009 | Jadrich et al. | |
| 7,495,227 B2 | 2/2009 | Hennessy et al. | |
| 7,569,831 B2 | 8/2009 | Jadrich et al. | |
| 7,582,877 B2 | 9/2009 | Dobrusskin et al. | |
| 7,745,797 B1 | 6/2010 | Liu et al. | |
| 7,800,065 B2 | 9/2010 | Konkle et al. | |
| 7,881,435 B2 | 2/2011 | Wu et al. | |
| 2005/0017188 A1 | 1/2005 | Yagi | |
| 2007/0072445 A1 | 3/2007 | Spahn | |
| 2007/0085015 A1 * | 4/2007 | Castleberry | 250/370.09 |
| 2008/0078940 A1 | 4/2008 | Castleberry et al. | |
| 2009/0122959 A1 | 5/2009 | Jadrich et al. | |
| 2010/0128850 A1 | 5/2010 | Konkle | |
| 2010/0264572 A1 | 10/2010 | Konkle | |
| 2011/0133085 A1 | 6/2011 | Konkle et al. | |
| 2011/0133096 A1 | 6/2011 | Konkle et al. | |
| 2011/0272588 A1 * | 11/2011 | Jadrich et al. | 250/370.11 |

* cited by examiner

*Primary Examiner* — Mark R Gaworecki
(74) *Attorney, Agent, or Firm* — Fletcher Yoder, P.C.

(57) ABSTRACT

A portable radiation detector is described having an elastomeric enclosure that provides some degree of mechanical shock resistance. In one embodiment, the enclosure encloses some or all of the electronic components of the detector and provides protection against drops and other mechanical shock for the enclosed components. One or more support or stiffening structures may also be provided to protect against impacts, to distribute static loads, and/or to impart a shape to the detector when handled.

19 Claims, 4 Drawing Sheets

MECHANICAL SHOCK ISOLATION FOR A RADIOGRAPHIC DEVICE

BACKGROUND

A number of non-invasive imaging approaches are known and are presently in use. One such type of system is based upon the detection of X-rays or other radiation that has passed through a volume of interest. The radiation traverses the volume, and whatever materials occupy the volume, and impact a film or a digital detector. In medical diagnostic contexts, for example, such systems may be used to visualize internal tissues and diagnose patient ailments. In other contexts, parts, baggage, parcels, and other materials may be imaged to assess their contents or for other purposes, such as for quality review in a manufacturing context.

Increasingly, such non-invasive imaging or inspection systems use digital circuitry, such as solid-state detectors, for detecting the radiation of interest. Such solid-state detectors may generate electrical signals indicative of the incident radiation on the detector, which in turn is indicative of the attenuation or scatter of the radiation along different ray paths through the imaged volume. The generated signals may in turn be processed to reconstruct images of the subject or object of interest within the volume, including internal features of an object or patient within the imaged volume.

Such solid-state or digital detectors may be portable and may be used in place of older detection systems (including film based detection systems) as a means of upgrading an existing system. In addition, in newer systems, a variety of portable detectors may be provided and used interchangeably with different systems, such that no one detector is fixed to or dedicated for use with a particular imaging system.

One drawback to a detector being portable and transportable is that the detector becomes subject to being dropped or damaged while being moved about a facility or between inspection or imaging locations. Further, to the extent that a portable digital detector is designed as a replacement for an existing detector implementation, the portable digital detector may be designed to conform to a form-factor or industry standard size associated with the existing detection scheme. In such a context, the space available within the detector to provide shock absorption or other physical protection of internal components may be limited due to adherence to the standardized size or shape of detector system being replaced.

BRIEF DESCRIPTION

In accordance with one embodiment, a portable radiation detector is provided. The portable radiation detector comprises a detector panel configured to generate signals in response to radiation incident on the detector panel. The portable radiation detector also comprises processing circuitry configured to acquire and process the signals generated by the detector panel. The portable radiation detector also comprises an elastomeric enclosure that is less rigid than the detector panel and which is disposed generally about the detector panel and processing circuitry.

In accordance with an additional embodiment, a radiation detector enclosure is provided. The enclosure comprises an elastomeric body. The elastomeric body comprises a first cavity configured to hold at least a detector panel and processing circuitry for reading out the detector panel and a second cavity configured to hold a radiation transparent window in a position above the first cavity.

In accordance with a further embodiment, a portable radiation detector is provided. The portable radiation detector comprises an elastomeric enclosure comprising one or more cavities. The portable radiation detector also comprises a detector panel and processing circuitry disposed within a first cavity of the elastomeric enclosure, wherein the detector panel is configured to generate one or more responsive signals in the presence of X-rays. The portable radiation detector also comprises an X-ray transparent window positioned over the detector panel on one surface of the elastomeric enclosure, wherein the X-ray transparent window is harder and stiffer than the elastomeric enclosure.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
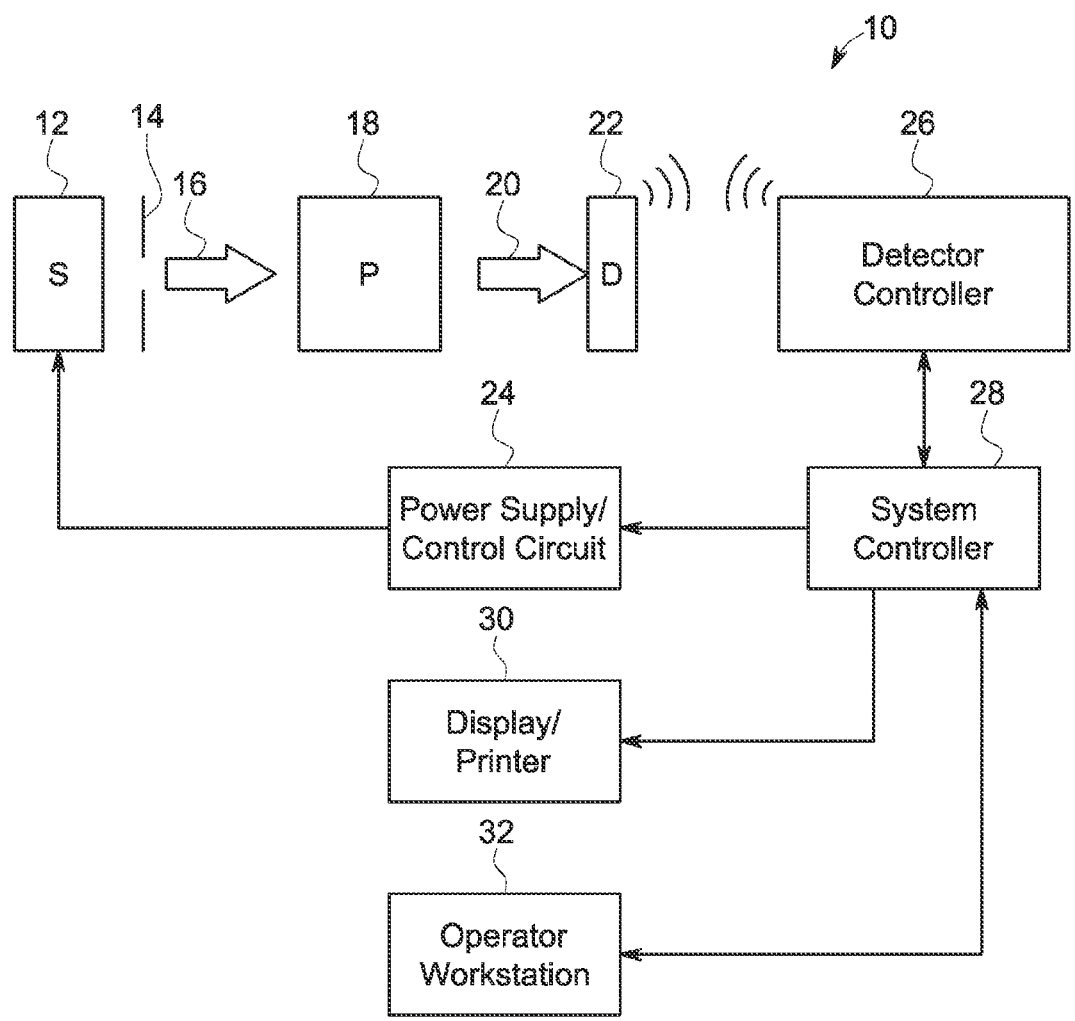
FIG. 1 is a diagrammatical overview of a digital radiation detection system in accordance with one or more embodiments of the present disclosure.

When introducing elements of various embodiments of the present disclosed subject matter, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

As discussed herein, portable digital radiation detectors (such as detectors suitable for detecting X-rays, gamma rays, radioactive isotopes, and so forth) may include an external elastomeric coating or case to provide a degree of mechanical shock protection. The elastomeric material used to form the coating or case is less rigid that a detector panel enclosed by the elastomeric material and can absorb shock delivered to the detector and/or may deform to allow distribution of static loads applied to the detector.

One or more specific embodiments of a portable detector having an elastomeric coating or case will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

With the foregoing comments in mind and turning to FIG. 1, this figure illustrates diagrammatically an example of an imaging or inspection system 10 for non-invasively acquiring and subsequently processing data related to incident radiation on a portable detector, such as portable detector having an elastomeric exterior, as discussed herein. In the illustrated embodiment, the system 10 is an X-ray based system designed both to acquire original image data and to process the image data for display. Though an X-ray based imaging system is discussed by way of example and to simplify explanation, in other implementations, other types of radiation of radioactive isotopes (such as gamma rays) may be measured or detected using a portable detector as discussed herein.

In the embodiment illustrated in FIG. 1, system 10 includes a source 12 of radiation, such as an X-ray tube, positioned adjacent to a collimator 14 that shapes and/or limits a stream of radiation 16 that passes into a region in which an object or subject, such as a patient 18, is positioned. In other embodiments, the source 12 of radiation 12 may be a radioactive isotope or other radiation emitter and structures such as collimator 14 may or may not be present to shape the emitted radiation stream.

A portion of the radiation 20 passes through or around the subject and impacts a portable digital radiation detector, represented generally at reference numeral 22. In the context of an X-ray based imaging or inspection system, the portable detector 22 may convert the X-ray photons incident on its surface to lower energy photons, and subsequently to electric signals, which are acquired and processed to reconstruct an image of the features within the subject. In other radiation detection contexts, the incident radiation may be converted to lower energy photons that may then be detected or, in a direct conversion implementation, the incident radiation itself may be measured without an intermediary conversion process.

In one example of an imaging or inspection system 10, the source 12 of radiation is a controlled source, which may be powered and/or controlled by a power supply/control circuit 24 which supplies both power and control signals for examination sequences. An example of one such controlled implementation is depicted in FIG. 1. In other implementations, the source 12 of radiation may not be a controlled source, but may instead be an uncontrolled source 12, such as a radioactive isotope or other source of radiation that is not powered and/or controlled directly.

In one example, the portable detector 22 is communicatively coupled to a detector controller 26 which commands acquisition of the signals generated in the portable detector 22. In the depicted example, the portable detector 22 communicates wirelessly with the detector controller 26 via a suitable wireless communication standard. In other embodiments, the portable detector 22 can communicate with the detector controller 26 over a wire or cable. In one implementation, the detector controller 26 may be implemented on a laptop computer or other suitable processor-based system suitable for communicating with the portable detector 22. For example, in certain implementations the detector controller 26 and/or other components of the system 10 may be implemented on or as part of a processor-based system, such as a desktop, laptop, or tablet computer platform.

In one embodiment, the detector controller 26 may be a handheld device or controller that allows a user to control operation of the portable detector 22, such as to place the detector 22 in a receptive state where incident radiation on the detector 22 may be measured or in a standby or idle state when an image operation is not currently being performed or is not imminent. In such implementations, the detector controller 26 may be controlled by a user, without further communication with the other components of the system 10. In other embodiments, the detector controller 26 may communicate with a system controller 28 and/or other components of the system 10, discussed below, to coordinate operation and readout of the portable detector 22 with the operation of the other components of the system 10.

In implementations in which a controlled source 12 is present, the respective power supply/control circuit 24 is responsive to signals from a system controller 28. In some implementations, the detector controller 26 may also be responsive to signals from the system controller 28. In general, the system controller 28 commands operation of the system 10 to execute examination protocols and, in some instances, to process acquired image data. For example, in some embodiments the system controller 28 may include signal processing circuitry, typically based upon a programmed general purpose or application-specific digital computer; and associated manufactures, such as optical memory devices, magnetic memory devices, or solid-state memory devices, for storing programs and routines executed by a processor of the computer to carry out various functionalities, as well as for storing configuration parameters and image data; interface protocols; and so forth. In one embodiment, a general or special purpose computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, the system controller 28 is linked to at least one output device, such as a display or printer as indicated at reference numeral 30. The output device may include standard or special purpose computer monitors and associated processing circuitry. One or more operator workstations 32 may be included in or otherwise linked to the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
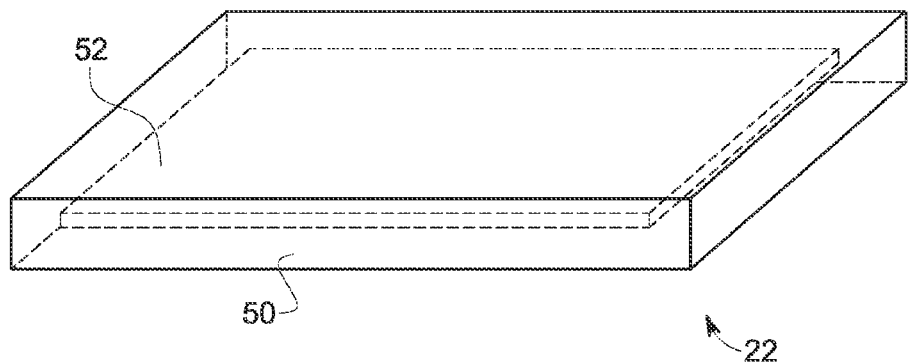
FIG. 2 is a perspective view of a portable digital detector, in accordance with aspects of the present disclosure.

With the foregoing discussion of imaging systems in mind, it should be appreciated that such systems may be used in conjunction with a portable detector 22, as discussed herein. One example of an embodiment of a portable detector 22 is generally illustrated in FIG. 2. In the illustrated embodiment, the portable detector 22 includes an elastomeric enclosure 50 that encloses various components 52 (e.g., the detector array or panel that generates signals in response to incident radiation, as well as the electronics used to operate the detector array) of the detector 22. In one embodiment, the elastomeric enclosure 50 is formed as a single piece around the components 52, such as by placing the components 52 in a suitable mold, blowing or injecting the unset elastomeric material into the mold so that the unset material flows around and over the components 52, and allowing the elastomeric material to set so as to form a single-piece or unitary enclosure about the components 52. In some embodiments, spacers may also be inserted into the mold or the mold may be designed so as to prevent the flow of elastomer between or over all of the components 52. For example, the molding process may be performed so as to leave air gaps or spaces between or around certain components of the detector 22.

Figure 3:
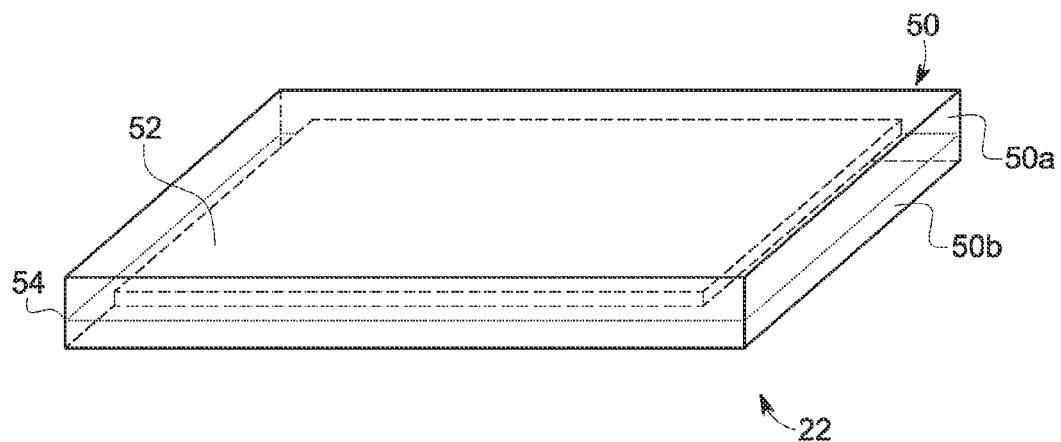
FIG. 3 is a perspective view of a portable digital detector, in accordance with further aspects of the present disclosure.

Turning to FIG. 3, in other embodiments the elastomeric enclosure 50 may be made of two or more separate elastomeric pieces (such as the first elastomeric piece 50a and second elastomeric 50b) that may be joined (such as at join line 54) to form the overall enclosure 50. For example, in one implementation, the separate pieces 50a, 50b may be separately molded, i.e., pre-molded, with one or both pieces formed to include spaces or cavities in which the components 52 may be securely fitted prior to joining the separate pieces 50a, 50b to form the overall enclosure 50.

In another implementation, one or both of the separate pieces 50a, 50b may be molded in the presence of some of the components 52 (such as the detector panel and/or other electronics) such that one or both of the separate pieces 50a, 50b are molded with one or more of the components 52 to be enclosed. In such an implementation, the separate pieces 50a, 50b may be fitted together to form the overall enclosure 50 with the components 52 protected inside the enclosure 50.

As will be appreciated, in implementations where the enclosure 50 is formed from initially separate pieces, the separate pieces may be joined together in various suitable ways to form the overall enclosure 50. For example, the separate pieces 50a, 50b may be formed to fit together by friction fit or via engagement of one or more engagement structures, such as complementary slots, tabs, divots, and so forth formed in the surface of the molded pieces. Likewise, mechanical fasteners (screws, staples, and so forth) or chemical fasteners (adhesive, epoxy, and so forth) may be used to secure the separate pieces together to form the overall enclosure 50. It should also be appreciated that, in implementations where the overall enclosure 50 is formed from separate pieces (e.g., pieces 50a, 50b), the engagement or fitting of the pieces together may be substantially permanent (i.e., the pieces are not intended to be separated again in the future) or temporary (i.e., the pieces may be separated as needed, such as to replace or service the components 52 within the enclosure 50. Similarly, certain of the cavities or spaces formed in the enclosure 50 may be formed on the external surfaces of the enclosure 50, such as to accommodate components that may be replaced or serviced over the life of the detector 22, such as a battery or other replaceable component.

With respect to the elastomeric material or materials that may be used to form the elastomeric enclosure 50, examples of suitable materials may be exhibit a durometer of 40 to 80 Shore A. Further, the elastomeric enclosure 50 is not necessarily uniform in durometer but may be softer or harder at different locations on the detector 22 and/or may be graded so as to gradually change in hardness from the surface of the enclosure 50 toward the interior of the enclosure 50. Examples of suitable materials for forming the elastomeric enclosure 50 include, but are not limited to, polyurethane, rubber, or ISOLOSS® LS, SL, or other isolating materials (available from 3M Company). Further, the exterior surface of the elastomeric enclosure may be treated or finished so as to be smooth or slippery (i.e., to have a low coefficient of friction, such as a coefficient of friction in the range of 0.1 to 0.3 between the enclosure and patient clothing or bedding) so as to facilitate placement of the detector 22 under a patient.

Figure 4:
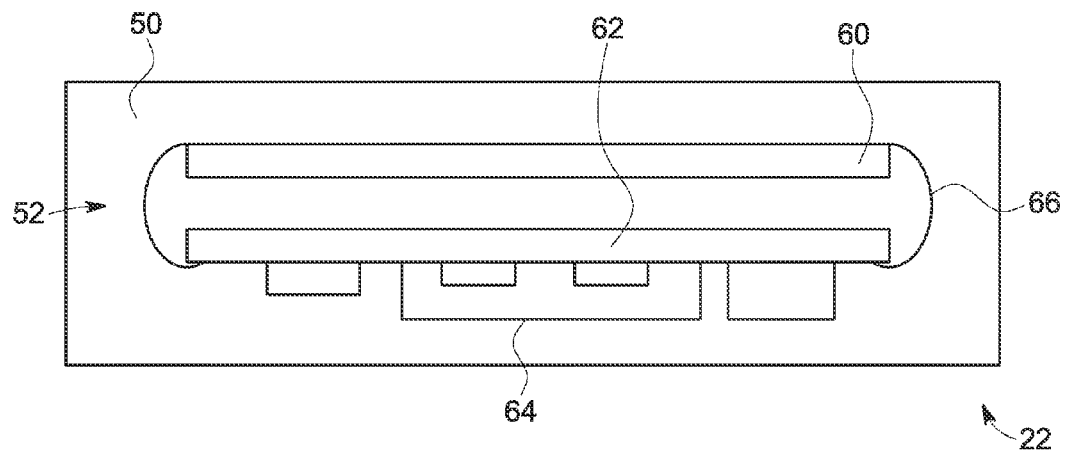
FIG. 4 is a cross-section view of an embodiment of a portable digital detector, in accordance with aspects of the present disclosure.

With the foregoing general discussion in mind, FIG. 4 depicts a cross-sectional view of one embodiment of the detector 22 having an elastomeric enclosure 50. In the depicted embodiment, the elastomeric enclosure 50 is molded (either as one-piece or multiple pieces) so as to fit around and to at least partially enclose components 52. In the depicted embodiment, the components 52 include an imager panel 60, processing circuitry 62, a battery 64, and readout electronics 66 (such as a flex circuit connecting the detector panel 60 and the processing circuitry 62). In other embodiments, additional components may be included or some of the listed components may be absent. For example, communication circuitry (e.g., wireless communication circuitry), light emitting diodes for visually conveying information to an operator, and/or interface structures (e.g., power buttons or other controls) may also be included in the detector 22 as part of the electronics 62 or as separate circuitry and may be partially or completely enclosed by the enclosure 50.

Because the elastomeric enclosure 50 is deformable and shock absorbent, it acts to protect the enclosed components 52 from mechanical shocks and drops. It should also be appreciated that, in certain embodiments, the elasticity of the enclosure 50 may allow controls (such as power switches, buttons, and so forth) to be actuated through the enclosure 50. For example, a user pressing on the appropriate location of the enclosure 50 above a button or switch may compress or deform the localized region of the enclosure 50 above the button or switch such that the button or switch to be actuated through the enclosure 50.

Figure 5:
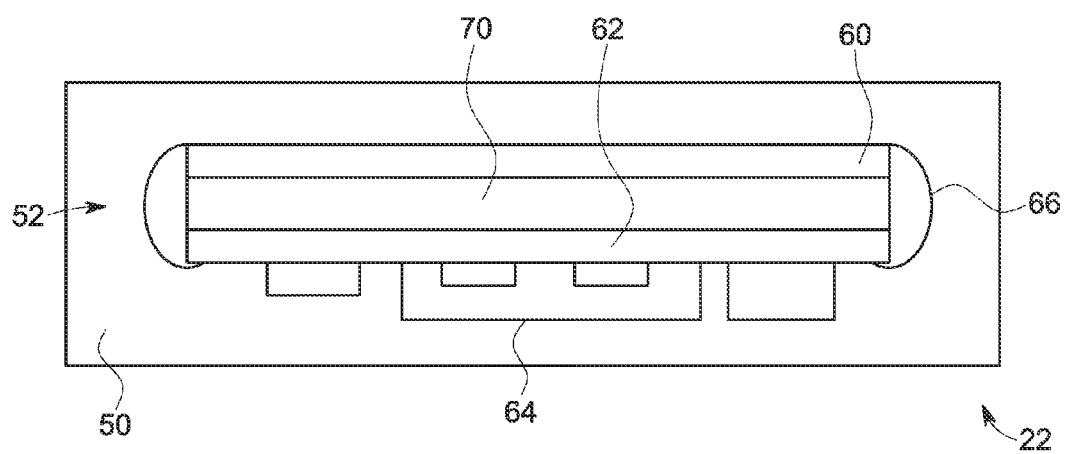
FIG. 5 is a cross-section view of an additional embodiment of a portable digital detector, in accordance with aspects of the present disclosure.

Turning to FIG. 5, in a further embodiment a rigid or semi-rigid support plate 70 is included in the detector 22. In such an embodiment, the detector panel 60 may be secured to the support plate 70 so as to prevent or limit deformation or flexure of the detector panel 60 when in use. That is, the enclosure 50 provides deformability and elasticity at the surface of the detector 22, such as to prevent from external mechanical shocks, while the support plate 70 limits the extent to which the overall detector 22 may be bent or deformed so as to prevent damage to the detector panel 60 or processing electronics 62 due to excessive bending or deformation.

Figure 6:
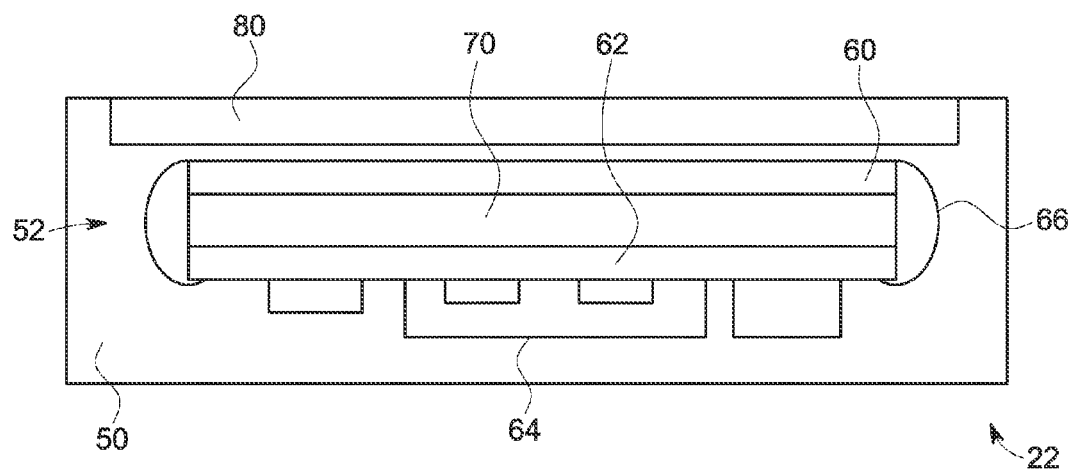
FIG. 6 is a cross-section view of a further embodiment of a portable digital detector, in accordance with aspects of the present disclosure.

Turning to FIG. 6, in a further embodiment, a radiation transparent window 80 (e.g., an X-ray transparent window) is added on one surface of the detector 22 above the detector panel 60. In one such implementation, the radiation transparent window 80 is stiff and is secured to the elastomeric enclosure 50 in front of the detector panel 60 so as to prevent or limit the detector panel 60 from point impacts and local loads. That is, the radiation transparent window is harder and stiffer than the elastomeric enclosure 50, and thus provides impact and load stress protection to the detector panel 60 that is distinct from the shock protection provided by the elastomeric enclosure 50. For example, the window 80 may help distribute a static load over the top surface of the detector 22, and thus may be useful in applications where such a load may be present, such as in imaging applications where a patient stands on the detector 22. In one implementation, the radiation transparent window may be carbon-fiber reinforced polymer.

In the depicted embodiment, the enclosure 50 is molded or formed so as to include a pocket or void sized to accommodate the radiation transparent window 80. In such an embodiment, the window 80 may be placed in the mold when the enclosure 50 is molded or may be added after the enclosure 50 is formed. If the window 80 is added after the enclosure 50 is molded, it may be secured to the enclosure 50 by friction fit, using complementary engagement structures (e.g., slots and tabs), using mechanical engagement structures (e.g., clips, screws, and so forth), or by using chemical bonding (e.g. adhesives or epoxy).

Figure 7:
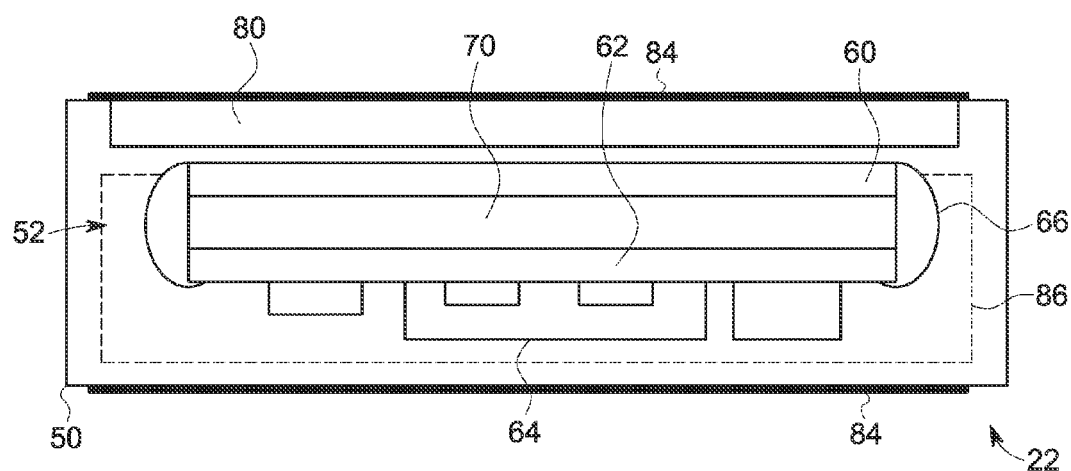
FIG. 7 is a cross-section view of an additional embodiment of a portable digital detector, in accordance with aspects of the present disclosure.

Turning to FIG. 7, in a further embodiment, a stiffening structure 86 is also included as part of the detector 22. For example, in one implementation, the stiffening structure 86 may be a framework, cage, or plane box formed of metal, plastic, or composite materials and which imparts form or stiffness to the detector 22. For example, in one embodiment, the stiffening structure 86 may provide rigidity that maintains the shape of the detector 22 when the detector 22 is picked up. In one such embodiment, the stiffening structure 86 may conform to the shape of the electronics 62 and/or detector panel 60.

In one implementation, the stiffening structure 86 is included in a mold during formation of the enclosure 50 so as to be integral to the enclosure 50 and detector 22. Alternatively, in an implementation in which the enclosure is assembled from two or more pre-molded pieces, the stiffening structure 86 may be adhered to or otherwise attached between the pre-molded pieces of the enclosure 50 during assembly of the detector 50. In an implementation in which a radiation transparent window 80 is present, the window 80 may be secured to one or both of the stiffening structure 86 or the enclosure 50. In addition, in certain implementations, the support plate 70, if present, may be attached to the stiffening structure 86.

In addition, the depicted embodiment of FIG. 7 includes one or more respective labels 84, such as polycarbonate labels, that may protect the surface of the detector 22 and/or provide information to a user of the detector 22. For example, such labels 84 may provide location markings useful in positioning the detector 22 with respect to a patient or imager. In addition, the labels 84 may provide a biocompatible and an aesthetically pleasing finish to the detector 22.

This written description uses examples to disclose the present subject matter, including the best mode, and also to enable any person skilled in the art to practice the disclosed subject matter, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A portable radiation detector, comprising:
 a detector panel configured to generate signals in response to radiation incident on the detector panel;
 processing circuitry configured to acquire and process the signals generated by the detector panel; and
 an elastomeric enclosure that is less rigid than the detector panel and which is disposed generally about the detector panel and processing circuitry, wherein the elastomeric enclosure has a durometer of 40 to 80 Shore A.

2. The portable radiation detector of claim 1, wherein the elastomeric enclosure is composed of two or more separately molded elastomeric pieces.

3. The portable radiation detector of claim 1, comprising:
 a battery configured to power one or both of the processing circuitry or the detector panel; and
 a flex circuit connecting the processing circuitry and the detector panel.

4. The portable radiation detector of claim 1, comprising:
 a power button that may be actuated through the elastomeric enclosure.

5. The portable radiation detector of claim 1, comprising a support plate on which the detector panel is mounted.

6. The portable radiation detector of claim 1, comprising a radiation transparent window fitted into the elastomeric enclosure above the detector panel.

7. The portable radiation detector of claim 1, comprising a stiffening structure within the elastomeric enclosure.

8. The portable radiation detector of claim 7, wherein the stiffening structure comprises a framework or cage formed of metal, plastic, or composite materials.

9. A radiation detector enclosure, comprising:
 an elastomeric body comprising:
  a first cavity configured to hold at least a detector panel and processing circuitry for reading out the detector panel; and
  a second cavity configured to hold a radiation transparent window in a position above the first cavity.

10. The radiation detector enclosure of claim 9, wherein the elastomeric body comprises two or more joined elastomeric pieces.

11. The radiation detector enclosure of claim 9, wherein the elastomeric body comprises at least one external cavity configured to hold a removable component.

12. The radiation detector enclosure of claim 9, wherein the elastomeric body comprises an external surface having a coefficient of friction between 0.1 and 0.3 when applied to patient clothing or bedding.

13. The radiation detector enclosure of claim 9, wherein the elastomeric body comprises polyurethane or rubber or a foam material.

14. A portable radiation detector, comprising:
 an elastomeric enclosure comprising one or more cavities, wherein the elastomeric enclosure has a durometer of 40 to 80 Shore A;
 a detector panel and processing circuitry disposed within a first cavity of the elastomeric enclosure, wherein the detector panel is configured to generate one or more responsive signals in the presence of X-rays; and
 an X-ray transparent window positioned over the detector panel on one surface of the elastomeric enclosure, wherein the X-ray transparent window is harder and stiffer than the elastomeric enclosure.

15. The portable radiation detector of claim 14, comprising a support plate on which the detector panel is mounted.

16. The portable radiation detector of claim 14, wherein the X-ray transparent window comprises carbon-fiber reinforced polymer.

17. The portable radiation detector of claim 14, comprising a stiffening structure disposed about the detector panel and processing circuitry.

18. The portable radiation detector of claim 14, comprising one or more labels provided on the surface of the elastomeric enclosure, wherein the labels provide location markings used to position the portable radiation detector.

19. A portable radiation detector, comprising:
 a detector panel configured to generate signals in response to radiation incident on the detector panel;
 processing circuitry configured to acquire and process the signals generated by the detector panel;
 an elastomeric enclosure that is less rigid than the detector panel and which is disposed generally about the detector panel and processing circuitry; and a power button that may be actuated through the elastomeric enclosure.

* * * * *